(12) United States Patent
Miyaji et al.

(10) Patent No.: US 7,342,048 B2
(45) Date of Patent: Mar. 11, 2008

(54) BIOABSORBABLE PHARMACEUTICAL FORMULATION

(75) Inventors: Tatsuaki Miyaji, Osaka (JP); Makoto Sato, Osaka (JP); Tamaki Murayama, Osaka (JP); Yohei Hoashi, Osaka (JP); Hisae Saito, Osaka (JP); Takao Okada, Kakogawa (JP); Yukari Imamura, Kakogawa (JP); Yoshimichi Fujiyama, Kakogawa (JP)

(73) Assignee: Nipro Corporation, Osaka (JP)

( * ) Notice: Subject to any disclaimer, the term of this patent is extended or adjusted under 35 U.S.C. 154(b) by 11 days.

(21) Appl. No.: 11/411,193

(22) Filed: Apr. 25, 2006

(65) Prior Publication Data

US 2006/0246139 A1  Nov. 2, 2006

(30) Foreign Application Priority Data

Apr. 28, 2005 (JP) ............................. 2005-131893

(51) Int. Cl.
*A61K 31/00* (2006.01)
*A61K 9/22* (2006.01)
*A01N 61/00* (2006.01)

(52) U.S. Cl. .................. 514/964; 514/1; 514/800; 424/426; 424/468

(58) Field of Classification Search .............. 514/1, 514/800, 964; 424/426, 468
See application file for complete search history.

(56) References Cited

U.S. PATENT DOCUMENTS

| 4,328,204 | A | 5/1982 | Wasserman et al. |
| 4,677,191 | A | 6/1987 | Tanaka et al. |
| 4,728,721 | A | 3/1988 | Yamamoto et al. |
| 4,767,628 | A | 8/1988 | Hutchinson |
| 4,789,726 | A | 12/1988 | Hutchinson |
| 5,585,460 | A | 12/1996 | Yamada et al. |
| 6,113,943 | A | 9/2000 | Okada et al. |
| 6,740,634 | B1 | 5/2004 | Saikawa et al. |
| 2002/0173467 | A1 | 11/2002 | Kamei et al. |
| 2003/0153724 | A1 | 8/2003 | Yamamoto et al. |
| 2004/0241229 | A1 | 12/2004 | Yamamoto et al. |
| 2006/0128938 | A1 | 6/2006 | Yamamoto et al. |

FOREIGN PATENT DOCUMENTS

| EP | 0 442 671 A2 | 8/1991 |
| EP | 0 839 525 A1 | 5/1998 |
| EP | 1 048 301 A1 | 11/2000 |
| EP | 1 310 517 A1 | 5/2003 |
| JP | S53-109930 A | 9/1978 |
| JP | S57-150609 A | 9/1982 |
| JP | S60-181029 A | 9/1985 |
| JP | S61-28521 A | 2/1986 |
| JP | 10-57098 B | 12/1998 |
| JP | 3168263 B | 5/2001 |
| JP | 3254449 B | 2/2002 |
| JP | WO 03/002091 * | 1/2003 |
| JP | 2003-206243 A | 7/2003 |
| JP | 2004-155792 A | 6/2004 |
| JP | 2004-256546 A | 9/2004 |

OTHER PUBLICATIONS

European Search Report for European Patent Application No. 06008539.6-2108 dated Oct. 5, 2006.

\* cited by examiner

*Primary Examiner*—Johann R. Richter
*Assistant Examiner*—Ernst V Arnold
(74) *Attorney, Agent, or Firm*—Kilyk & Bowersox, P.L.L.C.

(57) ABSTRACT

A bioabsorbable release-sustaining pharmaceutical formulation using a biodegradable release-sustaining base material which can prevent an effective component drug from being released too rapidly just after administration of the formulation and then allow continued release of the drug for at least one month at a defined rate, is provided. For the biodegradable release-sustaining base material, a lactic acid-glycolic acid copolymer (PLGA) with an adjusted distribution in molecular weight is used.

9 Claims, No Drawings

BIOABSORBABLE PHARMACEUTICAL FORMULATION

BACKGROUND OF THE INVENTION

1. Field of the Invention

The present invention relates to a bioabsorbable pharmaceutical formulation using a lactic acid-glycolic acid copolymer which is excellent as a biodegradable release-sustaining base material for a pharmaceutical formulation.

This application claims priority to JP patent application No. 2005-131893 filed Apr. 28, 2005.

2. Related Background of the Invention

Bioabsorbable pharmaceutical formulations have been designed and developed for: passive targets such as sustained drug efficacy, to alleviate side effects, to reduce the number of administrations of a drug with a short biological half life, and to reduce total dosages, and have been studied often as a means for drug delivery systems. For such a bioabsorbable pharmaceutical formulation, a release sustaining base material, namely a biodegradable polymer is used. For example, Patent Document No. 1 (as listed below) relates to a base material produced by the polycondensation of lactic acid and/or glycolic acid in the presence or absence of a catalyst; and Patent Document No. 2 relates to a method for manufacturing a sustained release type microcapsule using a biodegradable polymer. Various kinds of polymer compounds using lactic acid and glycolic acid have also been studied, for example, Patent Document No. 3 relates to a lactic acid-glycolic acid copolymer which has a weight-average molecular weight of 5,000 or more and 30,000 or less, is free from a catalyst, has a dispersion degree of 1.5 to 2, and has a lactic acid content of 50 to 95 wt % and a glycolic acid content of 50 to 5 wt %; and Patent Document No. 4 relates to a lactic acid-glycolic acid copolymer which has a weight-average molecular weight of 8,000 or more and 15,000 or less, and a ratio of approximately 1.90 or less between a weight-average molecular weight and a number-average molecular weight. Further, Patent Document No. 5 relates to a biodegradable aliphatic polyester which has a content of less than 3.0% for a low molecular polymer having a molecular weight of 1,000 or less.

In addition, Patent Document Nos. 6 and 7 relate to a distribution in molecular weight of a polymer suitable for a release sustaining base material; Patent Document No. 8 relates to a use of a release sustaining formulation using a lactic acid-glycolic acid copolymer (having an intrinsic viscosity of 1.38-0.10); Patent Document No. 9 relates to a method for preparing a release sustaining formulation with a copolymer of lactic acid-glycolic acid (having a molecular weight of 2,000-20,000); and Patent Document No. 10 relates to a use of a release sustaining formulation using a copolymer of lactic acid-glycolic acid (having an intrinsic viscosity of 0.3 or more).

As stated above, referring to a bioabsorbable pharmaceutical formulation and a polymer suitable for its base material, diverse technologies have been disclosed, but there is no pharmaceutical formulation furnished with sufficient performance which prevents an effective drug component from being released rapidly just after the administration of the formulation, thereby allowing continued release of the drug for at least a month at a defined rate. To provide such a formulation is an object of the present invention.

Patent Document No. 1: Publication No. JP S61-28521-A
Patent Document No. 2: Publication No. JP H01-57098-B
Patent Document No. 3: Patent No. JP 3168263 B
Patent Document No. 4: Publication No. JP 2003-206243-A
Patent Document No. 5: Patent No. JP 3254449 B
Patent Document No. 6: Publication No. JP 2004-155792-A
Patent Document No. 7: Publication No. JP 2004-256546-A
Patent Document No. 8: Publication No. JP S57-150609-A
Patent Document No. 9: Publication No. JP S60-181029-A
Patent Document No. 10: Publication No. JP S53-109930-A

SUMMARY OF THE INVENTION (Disclosure of the Invention)

(The Problems to be Solved by the Invention)

An object of the present invention is to provide a bioabsorbable pharmaceutical formulation which prevents an effective component drug from being released rapidly just after the administration of the formulation, thereby allowing continued release of the drug for at least a month at a defined rate.

[Means for Solving the Problem]

The present inventors made a detailed study to solve the above problem, and, as a result, have found that a lactic acid-glycolic acid copolymer with an adjusted distribution in molecular weight can be used as a biodegradable release-sustaining base material to solve the problem, and thus completed the present invention.

Therefore, various embodiments of the present invention are as follows:

1. A bioabsorbable pharmaceutical formulation comprising a lactic acid-glycolic acid copolymer and a drug, wherein the lactic acid-glycolic acid copolymer has the following fraction contents in percent of the total weight for their respective molecular weights determined by gel-permeation chromatography:

a fraction content of 0% to 5% for a molecular weight of 40,000 or more, a fraction content of 0.1% to 20% for a molecular weight of 16,000 or more and less than 40,000, a fraction content of 45% to 95% or more for a molecular weight of 5,000 or more and less than 16,000, a fraction content of 1% to 10%, preferably 5% to 10% for a molecular weight of 2,000 or more and less than 4,000, and a fraction content of 5% to 55%, preferably 5% to 10% for a molecular weight of 500 or more and less than 1,500.

2. The bioabsorbable pharmaceutical formulation according to claim 1, wherein the drug is a luteinizing hormone-releasing hormone (LH-RH) or a derivative thereof.

(Effects of the Invention)

The lactic acid-glycolic acid copolymer having the above fractions in molecular weight can be used to provide a bioabsorbable pharmaceutical formulation which prevents an effective component drug from being released rapidly just after the administration of the formulation, thereby allowing continued release of the drug from 1 month to 3 months at a defined rate. The formulation allows a drug to exist at an optimal therapeutic blood level in order to be effective in the body, within a range that is between the side effect expressing level and the minimum effective level, thereby resulting in a high effect based on a small dose (or frequency) of the pharmaceutical formulation that is administered.

DESCRIPTION OF THE PREFERRED EMBODIMENTS (Best Mode for Carrying Out the Invention)

The lactic acid-glycolic acid copolymer (hereinafter, sometimes referred to as "PLGA") of the present invention means a polymer which can have the following fraction contents for their respective molecular weights determined by gel-permeation chromatography (hereinafter, sometimes referred to as "GPC"): a fraction content of less than 5% for a molecular weight of 40,000 or more, a fraction content of less than 20% for a molecular weight of 16,000 or more and less than 40,000, a fraction content of 45% or more for a molecular weight of 5,000 or more and less than 16,000, a fraction content of less than 10% for a molecular weight of 2,000 or more and less than 4,000, and a fraction content of 5% or more for a molecular weight of 500 or more and less than 1,500. More preferably, the copolymer can have the following fraction contents: a fraction content of 0% or more and less than 5% for a molecular weight of 40,000 or more, a fraction content of less than 20% for a molecular weight of 16,000 or more and less than 40,000, a fraction content of 45% or more and less than 95% for a molecular weight of 5,000 or more and less than 16,000, a fraction content of less than 10% for a molecular weight of 2,000 or more and less than 4,000, and a fraction content of 5% or more and less than 20% for a molecular weight of 500 or more and less than 1,500.

The molecular weight described herein means a molecular weight in terms of polystyrene determined by GPC. Specifically, it means a molecular weight which is determined in terms of the molecular weights of polystyrenes used as reference materials: $6.77\times10^6$, $1.80\times10^6$, $9.0\times10^5$, $6.0\times10^5$, $2.33\times10^5$, $1.0\times10^5$, $5.0\times10^4$, $1.75\times10^4$, $9.0\times10^3$, $4.0\times10^3$, $2.0\times10^3$, $8.0\times10^2$, and $4.18\times10^2$, using GPC columns of TSLgel G6000HXL, G5000HXL, G4000HXL, G2500HXL, G1000HXL (7.8 mm I.D.×30 cm L) or TSK guard column HXL-H (all supplied by Tosoh Corporation) and a measurement device of HLC-8120 (supplied by Tosoh Corporation).

The lactic acid-glycolic acid copolymer described herein can include the lactic acid-glycolic acid copolymer or a salt thereof. As the salt, for example, a salt or a complex salt of the copolymer with an inorganic base including an alkali metal, such as sodium or potassium, and an alkaline earth metal such as calcium or magnesium, an organic base including an organic amine such as triethylamine and basic amines such as arginine, or a transition metal such as zinc, iron, or copper can be used. The lactic acid-glycolic acid copolymer can have preferably a compositional molar ratio of 90:10-40:60, and more preferably 70:30-80:20 of lactic acid to glycolic acid. The copolymer which has a glycolic acid content of 10 mole % or less is hydrolyzed too slowly to release a defined amount of a drug even one month after administration of the pharmaceutical formulation. In addition, the copolymer which has a glycolic acid content of beyond 60 mole % is low in solubility in an organic solvent that is generally used for a formulation, thereby creating an unfavorable effect brought about in the process for manufacturing the pharmaceutical formulation.

The lactic acid-glycolic acid copolymer of the present invention can be manufactured, but not limited to, by well known methods. For example, the method can include dehydration polycondensation from lactic acid and glycolic acid as cited in Polymeric Processing, 30(5), 208, (1981), or ring-opening polymerization from lactide and glycolide using a Lewis acid, a metal salt, an organometal and the like as a polymerization catalyst. A higher alcohol, a fatty acid and the like can also be used as an initiator.

Further, the lactic acid-glycolic acid copolymer characterized by fraction contents for the molecular weights according to the present invention can be obtained more efficiently by "two step polymerization" wherein a monomer such as lactic acid and glycolic acid, or an oligomer comprising lactic acid and glycolic acid is added in the course of polymerization to continue further polymerization. Alternatively, the polymer obtained by a well known method as described above including "two step polymerization" may be supplied to mix with at least two or more kinds of lactic acid-glycolic acid copolymers which are different in molecular weight and composition.

Further, the lactic acid-glycolic acid copolymer can be purified by well known methods, for example, by using an organic solvent. The organic solvent can be, for example, acetone, tetrahydrofuran, dioxane, dimethylformamide, dimethyl sulfoxide, methylene chloride, chloroform, hexane, methanol or combinations thereof. In particular, the combinations of methylene chloride, chloroform, methanol, hexane and the like are preferably used.

As a method for removing organic solvents, well known methods or modifications thereof can be used. The methods include a method wherein organic solvents are evaporated under a normal pressure or a gradually reduced pressure while stirring with a propeller stirrer, a magnetic stirrer or an ultrasonic generator, a method wherein organic solvents are evaporated under a controlled vacuum with a rotary evaporator and the like, a method wherein organic solvents are removed by heating under a reduced pressure using a vacuum dryer and the like, and a method wherein organic solvents are removed using a dialysis membrane.

Further, the lactic acid-glycolic acid copolymer having a distribution in molecular weight of the present invention can also be prepared by mixing at least two or more kinds of lactic acid-glycolic acid copolymers obtained by purification described above.

The bioabsorbable pharmaceutical formulation of the present invention means a release sustaining composition having an action which prevents an effective component drug from being released too rapidly just after the administration of the formulation, thereby allowing continued release of the drug for at least a month at a defined rate, thereby controlling the release of the drug with the sustained pharmacological effect. The formulation is not limited to an oral, injection, or transdermal formulation or the like, as long as it can sustain releasing a drug. The oral or injection formulation is preferred. The bioabsorbable pharmaceutical formulation can comprise well known pharmaceutically acceptable additives.

Releasing a drug at a defined rate described herein means that a bioabsorbable pharmaceutical formulation applied to a body continues releasing the effective component drug for at least one month. Specifically, the formulation can release the drug to give a residual rate of 90 to 100% on day 1, 65 to 85% on day 7, 50 to 70% on day 14, 40 to 60% on day 21, and 30 to 50% on day 28. The residual rate of a drug described herein can be determined as follows.

As a method for determining the residual rate of a drug in the present invention, a variety of well known methods can be used. For example, a high performance liquid chromatography can be used in accordance with a method for determining the residual rate of a drug, which is described in Journal of Controlled Release 28 (1994) 121-129, Chem. Pharm. Bull., 36, 1095 (1988), European Pharmacopoeia 4, and the like. For example, drug-supporting microspheres are suspended in 10 mL of 1/30 M phosphate buffer, pH 7.0 with 0.05% surfactant (Tween 80) contained, followed by rotating the suspension by a rotator at 25 cycle/min and filtering the microspheres by a Millipore filter having a pore size of 1 μm, and then the amount of a remaining drug is determined by a high performance liquid chromatography. The residual rate can be defined as a proportional percent of the amount of a remaining drug in the microspheres to an initial value, wherein the initial value is a drug content at an initial stage.

The drug comprised in a bioabsorbable pharmaceutical formulation of the present invention includes, but not limited to, a luteinizing hormone releasing hormone (LH-LR), analogs thereof, a thyroid hormone releasing hormone and salts and derivatives thereof. LH-RH or derivatives thereof can be used.

As an LH-RH derivative, an agonist or an antagonist of LH-RH may be used.

As an LH-RH antagonist, for example, biologically active peptides represented by the general formula (I) below or the salts thereof and the like can be used. General Formula (I):

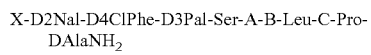

[wherein X represents N(4H$_2$-furoyl)Gly or NAc, A represents a residue selected from NMeTyr, Tyr, Aph(Atz), and NMeAph(Atz), B represents a residue selected from DLys (Nic), DCit, DLys(AzaglyNic), DLys(AzaglyFur), DhArg (Et2), DAph(Atz) and DhCi, and C represents Lys(Nisp), Arg or hArg(Et2)].

As an LH-RH agonist, for example, biologically active peptides represented by general formula (II) or salts thereof and the like can be used. General Formula (II):

[wherein Y represents a residue selected from DLeu, DAla, DTrp, DSer(tBu), D2Nal and DHis(ImBzl), Z represents NH—C$_2$H$_5$ or Gly-NH$_2$]. In particular, a peptide wherein Y represents DLeu, and Z represents NH—C$_2$H$_5$ (namely, a peptide represented by 5-oxo-Pro-His-Trp-Ser-Tyr-DLeu-Leu-Arg-Pro-NH—C$_2$H$_5$) or salts thereof (for example, acetates) can be used. More particularly, leuprorelin acetate can be used.

These peptides can be manufactured by methods, for example, shown in Patent Document No. 4.

The bioabsorbable pharmaceutical formulation of the present invention can be prepared by containing the above described drug in a biodegradable release sustaining base material of the present invention to microencapsulate. The microcapsule can be prepared by well known methods, for example, a W/O/W method described in Patent Document No. 4, a phase separation method, and a spray-drying method.

The drug is preferably contained in a biodegradable release sustaining base material at about 3-20 w/w %, and more preferably about 5-15 w/w %.

EXAMPLE

The present invention is described in detail, but is not limited to, by the following examples.

Example 1

In a reaction vessel having a inner volume of 300 ml equipped with a thermometer and a nitrogen inlet, 115 g of DL-lactic acid (supplied by Aldrich) and 25 g of glycolic acid (supplied by Aldrich) were added to react for 2.5 hours at 185° C. under a nitrogen stream at a flow rate of 200 mL/min, thereby to obtain reactant A having a weight-average molecular weight of 1500. To another reaction vessel having a inner volume of 300 ml equipped with a thermometer and an exhaust outlet, 228 g of DL-lactic acid and 52 g of glycolic acid were added to react for 40 hours at 185° C. under a reduced pressure from 10 to 1×10$^{-1}$ mmHg. Reactant A (15 g) was added therein to further react at 185° C. for 8 hours under a reduced pressure from 10 to 1×10$^{-1}$ mmHg. The obtained reactant was dissolved in methylene chloride to give a concentration of 10 w/v % and added in an approximately 6-fold volume of hexane by volume to deposit for purification, thereby to obtain 130 g of DL-lactic acid-glycolic acid copolymer (PLGA) as the base material for the present invention.

The molar ratio of the obtained copolymer was determined by H-NMR(1H-nuclear magnetic resonance spectra) to show that lactic acid:glycolic acid was 76:24. Further, this copolymer was determined and fractioned in molecular weight by GPC. The results are shown in Table 1.

In the present examples, the molecular weight determination by GPC was conducted under the following conditions.

Measurement apparatus: HLC-8120(supplied by Tosoh Corporation)

GPC column: the following six columns (supplied by Tosoh Corporation) were serially connected for use: TSK guard column HXL-H, TSLgel G1000HXL, G2500HXL, G4000HXL, G5000HXL, and G6000HXL.

Moving bed: tetrahydrofuran (flow rate 0.8 mL/min, temperature 40° C.)

Molecular weight reference material: polystyrenes of 6.77×10$^6$, 1.80×10$^6$, 9.0×10$^5$, 6.0×10$^5$, 2.33×10$^5$, 1.0×10$^5$, 5.0×10$^4$, 1.75×10$^9$, 9.0×10$^3$, 4.0×10$^3$, 2.0×10$^3$, 8.0×10$^2$, 4.18×10$^2$, 3.96 g of PLGA described above was measured and dissolved in 5 mL of dichloromethane to provide an oil phase.

0.45 g of leuprorelin acetate was dissolved in 0.5 mL of distilled water to provide an aqueous phase, in which the oil phase described above was then mixed and stirred by a small homogenizer (Polytron, Supplied by AG Kinematica) at 15,000 rpm to obtain a W/O emulsion. This W/O emulsion was added into 1 L of 0.1% aqueous solution of polyvinyl alcohol, emulsified again using a homogenizer (supplied by Hitachi, Ltd.) at 4,000 rpm to obtain a W/O/W emulsion. This W/O/W emulsion was gently stirred for approximately three hours to remove the solvent. After the removal of the solvent, the resultant was centrifuged to collect, washed with distilled water, supplied with 0.55 g of D-mannitol, dispersed again in a small amount of water, and then freeze-dried to yield 3.8 g of a microsphere powder.

Example 2

For the first step of polymerization, in a reaction vessel having an inner volume of 300 ml equipped with a thermometer and an exhaust outlet, 228 g of DL-lactic acid and 52 g of glycolic acid were added to react for 70 hours at 185° C. under a reduced pressure from 10 to 1×10$^{-1}$ mmHg. Next, for the second step of polymerization, 23 g of DL-lactic acid and 5 g of glycolic acid were added to react for another 5 hours at 185° C. under a reduced pressure from 10 to 1×10$^{-1}$ mmHg.

The copolymer obtained after the reaction was dissolved in chloroform to give a concentration of 10 w/v % and added in an approximately 6-fold volume of hexane to deposit for purification, thereby to obtain 120 g of PLGA as the base material for the present invention.

The molar ratio of the obtained copolymer was determined by H-NMR to show that lactic acid:glycolic acid was 75:25. Further, this copolymer was determined and fractioned in molecular weight by GPC. The results are shown in Table 1. The molecular weight was determined by the method described in EXAMPLE 1.

2.25 g of leuprorelin acetate was dissolved in 2.25 mL of distilled water to provide an aqueous phase. 19.8 g of PLGA described above was measured and dissolved in 20 mL of dichloromethane to provide an oil phase. The oil phase was added to mix in the aqueous phase, and then stirred and emulsified using a small homogenizer (Polytron, Supplied by AG Kinematica) at 15,000 rpm to obtain a W/O emulsion. This W/O emulsion was added into 5 L of 0.1% aqueous solution of polyvinyl alcohol at 19° C. and emulsified again using HOMOMIC LINE FLOW (supplied by Tokushukika co.) at 8,000 rpm to obtain a W/O/W emulsion. This W/O/W emulsion was gently stirred for approximately three hours to remove the solvent. After the removal of the solvent, microspheres were allowed to pass through a 75 µm sieve, centrifuged to collect, washed with distilled water, allowed to pass through a 95 µm sieve, supplied with 2.75 g of D-mannitol, dispersed again in a small amount of water, and then freeze-dried to obtain 13.97 g of a microsphere powder.

Example 3

Glycolic acid was dehydrogenated to polymerize at approximately 180° C. under stirring to obtain an oligomer, which was then subjected to vacuum distillation at 250° C. to obtain a glycolide.

In a reaction vessel having an inner volume of 300 ml equipped with a thermometer and an exhaust outlet, 245 g of DL-lactide (supplied by Tokyo Chemical Industry Co., Ltd.), 54 g of the glycolide and 12.4 g of DL-lactic acid were added, and then supplied with 0.03 g of zinc acetate (supplied by Kanto Chemical Co., INC.) as a catalyst. The resultant was allowed to react at 160° C. under a reduced pressure of $1\times10^{-1}$ mmHg for 98 hours to yield reactant B having a weight-average molecular weight of 10,900.

Next, in a reaction vessel having an inner volume of 300 ml equipped with a thermometer and a nitrogen inlet, 115 g of DL-lactic acid and 25 g of glycolic acid were added to react at 185° C. under a nitrogen stream at a flow rate of 200 mL/min for 2 hours, thereby to obtain reactant C having a weight-average molecular weight of 1,200.

The reactants B (140 g) and C (15 g) were dissolved in a solvent mixture of chloroform/acetone (1:1) to give a total concentration of 10 w/v %, extracted with an approximately 1.5-fold volume of a solvent mixture of methanol/water (1:1) to purify, and dried under vacuum to obtain 85 g of PLGA as the base material for the present invention.

The molar ratio of the obtained copolymer was determined by H-NMR to show that lactic acid:glycolic acid was 76:24. Further, this copolymer was determined and fractioned in molecular weight by GPC. The results are shown in Table 1. The molecular weight was determined by the method described in EXAMPLE 1.

4.5 g of leuprorelin acetate was dissolved in 5 mL of distilled water to provide an aqueous phase. 39.6 g of PLGA described above was measured and dissolved in 40 mL of dichloromethane to provide an oil phase. The oil phase was added to mix in the aqueous phase, and then stirred to emulsify using a small homogenizer (Polytron, Supplied by AG Kinematica) at 12,000 rpm to obtain a W/O emulsion. This W/O emulsion was added into 10 L of 0.1% aqueous solution of polyvinyl alcohol at 18° C. and emulsified again using HOMOMIC LINE FLOW (supplied by Tokushukika co.) at 7,000 rpm to obtain a W/O/W emulsion. This W/O/W emulsion was gently stirred for approximately three hours to remove the solvent. After the removal of the solvent, microspheres were allowed to pass through a 75 µm sieve, centrifuged to collect, washed with distilled water, allowed to pass through a 95 µm sieve, supplied with 4.72 g of D-mannitol, dispersed again in a small amount of water, and then freeze-dried to obtain 30.85 g of a microsphere powder.

Example 4

In a reaction vessel having an inner volume of 300 ml equipped with a thermometer and a nitrogen inlet, 38 g of DL-lactic acid and 9 g of glycolic acid were added to react at 185° C. under a nitrogen stream at a flow rate of 200 mL/min for an hour, and then dissolved in a solvent mixture of chloroform/acetone (1:1) to give a concentration of 10 w/v %, extracted with an approximately 1.5-fold volume of a solvent mixture of methanol/water (1:1) to purify, thereby to obtain reactant D having a weight-average molecular weight of 1,000.

In a similar reaction vessel, 150 g of DL-lactic acid and 32 g of glycolic acid were added to react at 185° C. under a nitrogen stream at a flow rate of 200 mL/min for 72 hours, dissolved in methylene chloride to give a concentration 10 w/v %, and deposited in an approximately 4-fold volume of methanol to purify, thereby to obtain reactant E having a weight-average molecular weight of 11,500.

The reactants E (140 g) and D (15 g) were added in methylene chloride to give a total concentration of 20 w/v % mixed, and then dried under vacuum to obtain 145 g of PLGA as a base material for the present material.

The molar ratio of the obtained copolymer was determined by H-NMR to show that lactic acid:glycolic acid was 72:28. Further, this copolymer was determined and fractioned in molecular weight by GPC. The results are shown in Table 1. The molecular weight was determined by the method described in EXAMPLE 1.

3.96 g of PLGA described above was measured and dissolved in 5 mL of dichloromethane to provide an oil phase.

0.45 g of leuprorelin acetate was dissolved in 0.5 mL of distilled water to provide an aqueous phase, in which the oil phase described above was then added to mix and emulsified under stirring by a small homogenizer (Polytron, Supplied by AG Kinematica) at 15,000 rpm to obtain a W/O emulsion. This W/O emulsion was added into 1 L of 0.1% aqueous solution of polyvinyl alcohol, emulsified again using a homogenizer (supplied by Hitachi, Ltd.) at 4,000 rpm to obtain a W/O/W emulsion. This W/O/W emulsion was gently stirred for approximately three hours to remove the solvent. After the removal of the solvent, the resultant was centrifuged to collect, washing with distilled water, supplied with 0.55 g of D-mannitol, dispersed again in a small amount of water, and then freeze-dried to yield 3.4 g of a microsphere powder.

TABLE 1

| | Distributions in molecular weight (%) | | | |
|---|---|---|---|---|
| | Example 1 | Example 2 | Example 3 | Example 4 |
| Weight-average molecular weight | 9,900 | 11,000 | 10,000 | 10,800 |
| Molecular weight fraction — over 40,000 | 0.2(%) | 0.2(%) | 0(%) | 0.4(%) |
| 16,000-40,000 | 12.7 | 17.0 | 13.7 | 19.6 |
| 5,000-16,000 | 60.8 | 64.9 | 68.3 | 60.7 |
| 2,000-4,000 | 9.2 | 5.7 | 5.9 | 5.2 |
| 500-1,500 | 8.1 | 5.6 | 5.1 | 7.9 |

COMPARATIVE EXAMPLE

In a reaction vessel having an inner volume of 300 ml equipped with a thermometer and an exhaust outlet, 228 g of DL-lactic acid and 52 g of glycolic acid were added to react for 30 hours at 185° C. under a reduced pressure from 10 to $1 \times 10^{-1}$ mmHg. The obtained reactant was dissolved in acetone to give a concentration of 20 w/v %, separated with an equal volume of distilled water, and further washed with a 5-fold volume of distilled water to purify.

The molar ratio of the obtained copolymer was determined by H-NMR to show that lactic acid:glycolic acid was 75:25. Further, this copolymer was determined and fractioned in molecular weight by GPC. The results are shown in Table 2. The molecular weight was determined by the method described in EXAMPLE 1.

4.5 g of leuprorelin acetate was dissolved in 5 mL of distilled water to provide an aqueous phase. 39.6 g of PLGA described above was measured and dissolved in 40 mL of dichloromethane to provide an oil phase. The oil phase was added to mix in the aqueous phase, and then emulsified under stirring by a small homogenizer (Polytron, Supplied by AG Kinematica) at 10,000 rpm to obtain a W/O emulsion. This W/O emulsion was added into 10 L of 0.1% aqueous solution of polyvinyl alcohol at 18° C. and emulsified again using HOMOMIC LINE FLOW (supplied by Tokushukika co.) at 8,000 rpm to obtain a W/O/W emulsion. This W/O/W emulsion was gently stirred for approximately three hours to remove the solvent. After the removal of the solvent, microspheres were allowed to pass through a 75 μm sieve, centrifuged to collect, washed with distilled water, allowed to pass through a 95 μm sieve, supplied with 3.2 g of D-mannitol, dispersed again in a small amount of water and then freeze-dried to obtain 17.2 g of a microsphere powder.

Experimental Example 1

Measurement of the Residual Rate of a Drug 50 mg of the resulting microspheres obtained in the Examples and Comparative Example were suspended in 10 mL of 1/30 M phosphate buffer comprising 0.05% Tween80, pH7.0. These suspensions were rolled by a rotator at 25 cycles/min to centrifuge the microspheres, which were then filtered by a 1 μm Millipore filter to collect.

The collected microspheres were dissolved in 10 mL of dichloromethane, extracted with 20 mL of 1/30 M phosphate buffer, followed by measuring the remaining leuprorelin acetate by a HPLC (L-2000, Hitachi, Ltd.). Mightysil (150 mm×4.6 mm, Kanto Chemical Co., INC.) was used for the column, the columns were set to have a constant temperature of around 30° C., 1/30 M phosphate buffer/acetonitrile (3:1) was used for a mobile phase, and an ultraviolet-visible absorptiometer (wavelength:280 nm) was used as a detector.

The initial drug content is defined as an initial value, and on days 1, 7, 14, 21, and 28 after the microspheres were stored, the percentages in amount of the drug (leuprorelin acetate) in the microspheres to the initial value were determined as the residual rates of the drug.

The measurement results of the residual rates of the drug are shown in Table 3.

TABLE 2

| Distributions in molecular weight (%) | |
|---|---|
| | Comparative Example 1 |
| Weight-average molecular weight | 10,900 |
| Molecular weight fraction — 40,000< | 1.1(%) |
| 16,000-40,000 | 22.7 |
| 5,000-16,000 | 52.3 |
| 2,000-4,000 | 11.7 |
| 500-1,500 | 3.4 |

TABLE 3

Results of a drug release test (Rates of residual drug (%))

| | Day 1 | Day 7 | Day 14 | Day 21 | Day 28 |
|---|---|---|---|---|---|
| Example 1 | 94.2 | 74.2 | 62.7 | 55.0 | 41.2 |
| Example 2 | 92.9 | 80.1 | 68.1 | 58.1 | 44.5 |
| Example 3 | 95.0 | 73.6 | 63.2 | 51.9 | 41.4 |
| Example 4 | 92.8 | 77.4 | 66.0 | 55.0 | 44.4 |
| Comparative Example 1 | 86.9 | 63.0 | 51.7 | 40.5 | 30.8 |

From the results shown in Table 3, it is demonstrated that the lactic acid-glycolic acid copolymer (PLGA) having the molecular weight fractions of the present invention can be used to prevent a drug from being rapidly released, especially on a daily basis, as compared to PLGA of the comparative example.

INDUSTRIAL APPLICABILITY

As explained above, the lactic acid-glycolic acid copolymer having the molecular weight fractions of the present invention can be used to provide a bioabsorbable pharmaceutical formulation which allows to restrain or prevent an effective component drug from being released rapidly just after the administration of the formulation and then continue releasing the drug for at least a month at a defined rate. The formulation allows a drug to exist at an optimal therapeutic blood level (at a therapeutic concentration of the blood) in order to be effective in the body, within a range that is between the side effect expressing level and the minimum effective level, thereby resulting in a high effect based on a small dose (or frequency) of the formulation that is administered. Such a pharmaceutical formulation can be applied to lower the administration frequency, allowing exemption of a patient from the burden of suffering multiple administrations. In addition, the formulation can prevent a drug from being released too rapidly just after the administration, thereby allowing effective utilization of the drug to be free from the side effect and from the wasteful dosage.

What is claimed is:

1. A bioabsorbable pharmaceutical formulation comprising a lactic acid-glycolic acid copolymer and a drug, wherein the lactic acid-glycolic acid copolymer has the following fraction contents for their respective molecular weights determined by gel-permeation chromatography:

a fraction content of 0% to less than 5% for a molecular weight of 40,000 or more, a fraction content of 0.1% to less than 20% for a molecular weight of 16,000 or more and less than 40,000, a fraction content of 45% or more for a molecular weight of 5,000 or more and less than 16,000, a fraction content of 1% to less than 10% for a molecular weight of 2,000 or more and less than 4,000, and a fraction content of 5% or more for a molecular weight of 500 or more and less than 1,500.

2. The bioabsorbable pharmaceutical formulation according to claim 1, wherein the drug is a luteinizing hormone-releasing hormone, a salt of a luteinizing hormone-releasing hormone, an agonist of a luteinizing hormone-releasing hormone, or an antagonist of a luteinizing hormone-releasing hormone.

3. The bioabsorbable pharmaceutical formulation according to claim 1, wherein the fraction content for the molecular weight of 5,000 or more and less than 16,000 is 45% to 95%, and the fraction content for the molecular weight of 500 or more and less than 1,500 is 5 to 55%.

4. The bioabsorbable pharmaceutical formulation according to claim 1, wherein the lactic acid-glycolic acid copolymer comprises a salt of lactic acid-glycolic acid copolymer.

5. The bioabsorbable pharmaceutical formulation according to claim 1, wherein the lactic acid-glycolic acid copolymer is obtained by two step polymerization.

6. The bioabsorbable pharmaceutical formulation according to claim 1, wherein the lactic acid-glycolic acid copolymer has a compositional molar ratio of from about 90:10 to about 40:60 of lactic acid to glycolic acid.

7. The bioabsorbable pharmaceutical formulation according to claim 6, wherein the lactic acid-glycolic acid copolymer has a compositional molar ratio of from about 70:30 to about 80:20 of lactic acid to glycolic acid.

8. The bioabsorbable pharmaceutical formulation according to claim 1, wherein the lactic acid-glycolic acid copolymer is purified by an organic solvent.

9. The bioabsorbable pharmaceutical formulation according to claim 1, wherein the drug is a thyroid hormone-releasing hormone, a salt of a thyroid hormone-releasing hormone, an agonist of thyroid hormone-releasing hormone, or an antagonist of thyroid hormone-releasing hormone.

* * * * *